United States Patent [19]

Grollier et al.

[11] Patent Number: 4,892,888

[45] Date of Patent: * Jan. 9, 1990

[54] ANHYDROUS COMPOSITION, STABLE TO OXIDATION, OF ANTHRALIN OR ONE OF ITS DERIVATIVES IN A FATTY ACID ALKYL ESTER AND ITS USE IN THE TREATMENT OF SKIN DISEASES

[75] Inventors: Jean-François Grollier, Paris; Georges Rosenbaum, Asnieres; Josiane Allec, Pierrefitte; Braham Shroot, Antibes, all of France

[73] Assignee: Société Anonyme dite: L'Oreal, Paris, France

[ * ] Notice: The portion of the term of this patent subsequent to Jan. 22, 2002 has been disclaimed.

[21] Appl. No.: 175,602

[22] Filed: Mar. 31, 1988

Related U.S. Application Data

[63] Continuation of Ser. No. 435,984, Oct. 22, 1982, abandoned.

[30] Foreign Application Priority Data

Oct. 23, 1981 [FR] France .................................. 81 19952
Apr. 5, 1982 [FR] France .................................. 82 05864

[51] Int. Cl.$^4$ ............................................. A61K 31/05
[52] U.S. Cl. .................................... 514/132; 514/863; 514/970

[58] Field of Search ........................ 514/732, 863, 970

[56] References Cited

U.S. PATENT DOCUMENTS 4,299,826 11/1981 Luedders ............................ 424/181
4,367,224 1/1983 Van Scott et al. .................. 424/174

OTHER PUBLICATIONS

Remington's Pharmaceutical Sciences, 16th ed. 1980, p. 356.
Cosmetics, Science & Technology (Balsam et al) 2nd ed, vol. 1, pp. 194–195 (1972).
Chemical Abstracts 76:144782y (1972).

*Primary Examiner*—Leonard Schenkman
*Attorney, Agent, or Firm*—Wegner & Bretschneider

[57] ABSTRACT

Anhydrous composition of anthralin or a derivative thereof which is stable to oxidation.

This composition is in the form of a solution or dispersion of anthralin or a derivative thereof in at least one fatty acid alkyl ester, the fatty acid having 5 to 18 carbon atoms and the alkyl radical having 4 to 18 carbon atoms.

This composition is used in the treatment of skin diseases, particularly psoriasis.

3 Claims, No Drawings

ANHYDROUS COMPOSITION, STABLE TO OXIDATION, OF ANTHRALIN OR ONE OF ITS DERIVATIVES IN A FATTY ACID ALKYL ESTER AND ITS USE IN THE TREATMENT OF SKIN DISEASES

This application is a continuation of U.S. application Ser. No. 435,984, filed Oct. 22, 1982, abandoned.

The present invention relates to an anhydrous composition, stable to oxidation, of anthralin or one of its derivatives, and to its use for the treatment of skin diseases and in particular for the treatment of acne, warts, and especially psoriasis.

Psoriasis is a particularly frequent form of dermatosis which manifests itself as lesions found on the elbows, on the back of the forearms, on the knees, on the legs and in the sacro-lumbar regions, as well as on the scalp.

Amongst the various substances which have already been recommended for the treatment of psoriasis, special mention must be made of anthralin or dithranol (1,8,9-trihydroxyanthracene), which has proved particularly active, but the use of which is not without certain disadvantages insofar as this compound is very readily degraded by oxidation to give dark-coloured polymeric products capable of staining the skin and clothes.

In order to prevent degradation, it has been proposed to use, as vehicle, vaseline in association with certain antioxidants, but it has been shown that anthralin is dispersed in vaseline, but not solubilized. Furthermore, vaseline-based products are very difficult to remove from the scalp.

It has now been found that it is possible to preserve anthralin or a derivative thereof under excellent conditions by using certain fatty acid esters as the vehicle, without it being necessary to resort to the use of stabilizing compounds or antioxidants, such as α-hydroxyacids.

Experiments on preservation have in fact made it possible to show that no degradation due to atmospheric oxygen is detectable, the coloration of the solution remaining constant or essentially constant; physico-chemical determinations confirm this good stability.

The present invention has as an object, as a new industrial product, an anhydrous composition, which is stable to oxidation, containing anthralin or one of its derivatives, for the treatment of skin diseases, in particular psoriasis, this composition being in the form of a solution or dispersion of anthralin or one of its derivatives in at least one fatty acid alkyl ester, the fatty acid having from 5 to 18 carbon atoms and the alkyl radical, which is branched or unbranched, having from 4 to 18 carbon atoms.

Amongst the esters corresponding to the above definition, there may be mentioned isodecyl neopentanoate, cetyl octanoate, stearyl octanoate, 2-ethylhexyl palmitate, butyl stearate, 2-ethylhexyl stearate, isocetyl stearate and mixtures thereof.

Amongst the anthralin derivatives which can also be stabilized by fatty acid alkyl esters, there may be mentioned the compounds described in French Patent Application Nos. 80/22,454 and 80/22,455.

According to the invention, the concentration of anthralin or one of its derivatives in the composition is generally between 0.01 and 5%, but preferably between 0.1 and 3%.

The composition according to the invention can be used as such in the local treatment of skin diseases and in particular psoriasis, but is preferably employed in a mixture with 0.1 to 20% by weight of a thickener which does not modify the stability and which is a silica or a polyethylene powder.

In fact, it is advantageous to use relatively thick compositions in order to prevent any flowing and thus to prevent irritation phenomena on the healthy parts of the skin.

Amongst the silicas which can be used according to the invention, there may be mentioned those having an average particle diameter of less than 30 m$\mu$, and especially the silicas sold under the names "AEROSIL 200" and "AEROSIL R 972" by DEGUSSA or those sold under the name "HDK," in particular the silica "HDK N 20 E," by WACKER, these silicas being used by themselves or in a mixture.

Amongst the polyethylene powders which can be used according to the invention, there may be mentioned:

(1) The polyethylene powders of the low-density type havng a melting point of 104°–113° C., determined by the ASTM method D 2117-64, and a density at 23° C. of 0.914 to 0.923 (g/cm$^3$), determined by the ASTM method D 2839. As examples of polyethylene powders possessing these characteristics, there may be mentioned those sold under the names "LOTRENE UA 7000 S" and "LOTRENE UA 4000 S" by C. D. F. Chimie.

(2) The polyethylene powders of the high-density type having a softening point of 128°–129° C., determined by the ASTM method E 28, and a density of 0.96 (g/cm$^3$), determined by the ASTM method D 1505. As examples of polyethylene powders possessing these characteristics, there may be mentioned those sold under the names "Polymist B6" and "Polymist B12" by ALLIED CHEMICAL.

(3) The polyethylene powders having a softening point of 102°–117° C., determined by the ASTM method E 28, and a density of 0.90 to 0.94 (g/cm$^3$), determined by the ASTM method D 1505. As an example of a polyethylene powder possessing these characteristics, there may be mentioned that sold under the name "Polyethylene AC 6A" by ALLIED CHEMICAL.

(4) The ethylene/acrylic acid copolymers having a softening point of 92°–108° C., determined by the ASTM method E 28, and a density of 0.93 (g/cm$^3$), determined by the ASTM method D 1505. As an example of a powder possessing these characteristics, there may be mentioned that sold under the name "Polyethylene AC 540" by ALLIED CHEMICAL.

Other ingredients can be introduced into the compositions, for example oils, waxes, salicylic acid as well as any other ingredient which is generally present in compositions intended for topical application, insofar as these ingredients do not have adverse effects on the stability.

Several non-limiting examples of compositions according to the invention based on anthralin or one of its derivatives will now be given for purposes of illustration.

EXAMPLE 1

A pre-shampoo composition is prepared according to the invention by mixing the following ingredients:

| | |
|---|---|
| Anthralin | 0.4 g |
| Salicylic acid | 0.4 g |

-continued

| | |
|---|---|
| 50:50 mixture of cetyl octanoate and stearyl octanoate q.s. | 100 g |

EXAMPLE 2

A pre-shampoo composition is prepared according to the invention by mixing the following ingredients:

| | |
|---|---|
| Anthralin | 0.1 g |
| Isocetyl stearate q.s. | 100 g |

EXAMPLE 3

A gel for the skin is prepared according to the invention by mixing the following ingredients:

| | |
|---|---|
| Anthralin | 0.4 g |
| Silica "HDK N 20 E" (pyrogenic silica sold by WACKER) | 7.0 g |
| Isocetyl stearate q.s. | 100 g |

EXAMPLE 4

A gel for the skin is prepared according to the invention by mixing the following ingredients:

| | |
|---|---|
| Anthralin | 3 g |
| Aerosil R 972 | 8 g |
| Salicylic acid | 0.2 g |
| 2-Ethylhexyl palmitate q.s. | 100 g |

EXAMPLE 5

A gel for the skin is prepared according to the invention by mixing the following ingredients:

| | |
|---|---|
| Anthralin | 5 g |
| Aerosil 200 | 8 g |
| Cetyl octanoate q.s. | 100 g |

In this example, the Aerosil 200 can be replaced by the same amount of the silica HDK N 20 E.

EXAMPLE 6

A gel for the skin, for the treatment of psoriasis, is prepared according to the invention by mixing the following ingredients:

| | |
|---|---|
| Anthralin | 1 g |
| Polyethylene AC 6A | 7.5 g |
| Stearyl octanoate q.s. | 100 g |

In Examples 4 to 6 above, the fatty acid alkyl ester used can be replaced by an equivalent amount of cetyl octanoate or 2-ethylhexyl stearate.

EXAMPLE 7

A stick for the skin, intended for the local treatment of psoriasis, is prepared according to the invention by mixing the following ingredients:

| | |
|---|---|
| Anthralin | 0.5 g |
| Cocoa butter | 12.5 g |
| Ozokerite wax | 18.75 g |
| White paraffin | 6.25 g |
| White vaseline | 12.50 g |
| 70:30 mixture of cetyl octanoate and stearyl octanoate q.s. | 100 g |

EXAMPLE 8

A gel for the skin, for the treatment of psoriasis, is prepared according to the invention by mixing the following ingredients:

| | |
|---|---|
| Anthralin | 1 g |
| Polyethylene AC 540 | 7.5 g |
| 2-Ethylhexyl stearate q.s. | 100 g |

When applied to parts of the skin or scalp in an amount sufficient to cover the lesions, compositions 1 to 8 above make it possible, after a treatment period of 3 to 5 weeks, to effect a regression and cure of the skin diseases, in particular psoriasis.

We claim:

1. A thickened and stable to oxidation, anhydrous composition for the treatment of diseases of the skin and particularly for psoriasis containing 0.01 to 5% by weight of anthralin in the form of a solution or dispersion of anthralin in a carrier comprising a fatty acid alkyl ester, the fatty acid having from 5 to 18 carbon atoms and the alkyl radical having from 4 to 18 carbon atoms, said fatty acid alkyl ester stabilizing said anthralin, and of 0.1 to 20% by weight of a thickener, said thickener being a silica having an average particle diameter of less than 30 m$\mu$.

2. The composition of claim 1 wherein the fatty alkyl ester is selected from the group consisting of isodecyl neopentanoate, cetyl octanoate, stearyl octanoate, 2-ethylhexyl palmitate, butyl stearate, 2-ethylhexyl stearate, isocetyl stearate and mixtures thereof.

3. A process for the treatment of skin diseases particularly psoriasis in which an effective amount of the composition of claim 1 is applied to the lesions to be treated.

* * * * *